United States Patent
Saeedkia

(10) Patent No.: US 9,239,286 B2
(45) Date of Patent: Jan. 19, 2016

(54) METHODS AND APPARATUS FOR IDENTIFYING AND SORTING MATERIALS USING TERAHERTZ WAVES

(71) Applicant: TETECHS INC., Waterloo (CA)

(72) Inventor: Daryoosh Saeedkia, Waterloo (CA)

(73) Assignee: Tetechs Inc., Waterloo, Ontario (CA)

( * ) Notice: Subject to any disclaimer, the term of this patent is extended or adjusted under 35 U.S.C. 154(b) by 0 days.

(21) Appl. No.: 14/363,562

(22) PCT Filed: Dec. 11, 2012

(86) PCT No.: PCT/CA2012/001137
§ 371 (c)(1),
(2) Date: Jun. 6, 2014

(87) PCT Pub. No.: WO2013/086608
PCT Pub. Date: Jun. 20, 2013

(65) Prior Publication Data
US 2014/0367316 A1    Dec. 18, 2014

Related U.S. Application Data

(60) Provisional application No. 61/569,264, filed on Dec. 11, 2011.

(51) Int. Cl.
*B07C 5/34* (2006.01)
*G01N 21/25* (2006.01)
(Continued)

(52) U.S. Cl.
CPC ............... *G01N 21/255* (2013.01); *B07C 5/34* (2013.01); *B07C 5/342* (2013.01); *B07C 5/344* (2013.01);
(Continued)

(58) Field of Classification Search
CPC ........ B07C 5/342; B07C 5/3416; B07C 5/34; B07C 5/344; G01N 21/3581
See application file for complete search history.

(56) References Cited

U.S. PATENT DOCUMENTS 5,260,576 A * 11/1993 Sommer et al. ............ 250/359.1
5,794,788 A    8/1998 Massen
(Continued)

FOREIGN PATENT DOCUMENTS

EP    0441012    8/1991
WO    00/50859    8/2000
(Continued)

OTHER PUBLICATIONS

International Searching Authority, International Search and Written Opinion for PCT/CA2012/001137, mailed on Feb. 18, 2013.
(Continued)

*Primary Examiner* — Luis A Gonzalez
(74) *Attorney, Agent, or Firm* — Bereskin & Parr LLP/S.E.N.C.R.L., s.r.l.

(57) ABSTRACT

A terahertz-based material identification system includes a terahertz source for transmitting a terahertz wave for interaction with an object. The interaction results in a resulting terahertz wave that is influenced by the object. A terahertz detector receives the resulting terahertz wave and is configured to output measurement data corresponding to the resulting terahertz wave. A processor is in communication with the terahertz detector for receiving the measurement data. The processor is also configured to calculate an object response signature based on the measurement data, and compare the object response signature to a set of known response signatures so as to identify the object. The material identification system may also be implemented as part of a sorting system that is configured to selectively separate the object from a mixture based on the identity of the object.

20 Claims, 14 Drawing Sheets

(51) Int. Cl.
  *B07C 5/342* (2006.01)
  *B07C 5/344* (2006.01)
  *G01N 21/3581* (2014.01)
  *G01N 21/3563* (2014.01)
  *G01N 33/44* (2006.01)
  *G01N 21/84* (2006.01)

(52) U.S. Cl.
  CPC .......... *B07C 5/3416* (2013.01); *G01N 21/3563* (2013.01); *G01N 21/3581* (2013.01); *G01N 33/442* (2013.01); *G01N 2021/845* (2013.01)

(56) References Cited

U.S. PATENT DOCUMENTS

| | | | |
|---|---|---|---|
| 2004/0155665 | A1 | 8/2004 | Arnone et al. |
| 2006/0022140 | A1 | 2/2006 | Connelly et al. |
| 2006/0255277 | A1 | 11/2006 | Cole et al. |
| 2010/0202694 | A1* | 8/2010 | Kabumoto et al. .......... 382/190 |
| 2010/0230327 | A1* | 9/2010 | Hartrumpf et al. .......... 209/577 |
| 2012/0217403 | A1 | 8/2012 | Sartorius et al. |

FOREIGN PATENT DOCUMENTS

| | | |
|---|---|---|
| WO | 03/023383 A2 | 3/2003 |
| WO | 2011/050959 A1 | 5/2011 |
| WO | 2011/094564 A2 | 8/2011 |

OTHER PUBLICATIONS

Ferguson et al., "Materials for terahertz science and technology", Nature Materials, vol. 1, p. 26-33, Sep. 2002.

Jansen et al., "Applications for THz Systems", Optik & Photonik, vol. 3, No. 4, pp. 26-30, Dec. 2008.

Wietzke et al., "Applications of terahertz spectroscopy in the plastics industry", Terahertz Photonics, Proc. of SPIE, vol. 6840, Jan. 4, 2007.

Database Inspect (Online), The Insitution of Electrical Engineers, Stevenage, GB; Jul. 2010, Wang He et al: Terahetz Spectroscopic inspection of Several Kinds of Plastic, XP00274085, Acta Photonica Sinica Science Press China, vol. 39, No. 7, Jul. 2020, pp. 1185-1188, ISSn: 1004-4213, DOI: 10.3788/GZXB20103907.1185.

European Patent Office, Extended European Search Report for application No. 12858279.8, Jul. 28, 2015.

* cited by examiner

METHODS AND APPARATUS FOR IDENTIFYING AND SORTING MATERIALS USING TERAHERTZ WAVES

PRIORITY

This application claims the benefit of U.S. Provisional. Patent Application Ser. No. 61/569,264 filed on Dec. 11, 2011, by the present inventor, and entitled "TERAHERTZ SENSORS FOR MATERIAL SORTING APPLICATIONS", the entire contents of which are hereby incorporated by reference herein for all purposes.

FIELD

The embodiments disclosed herein relate to techniques for identifying, sorting, and separating materials, and in particular to such methods and apparatus for sorting plastic materials for recycling purposes.

BACKGROUND

Material sensing, identification, and classification can be a challenge in many industries, such as electronic-waste and municipal waste recycling, chemical supplying, and pharmaceutical manufacturing, to name a few.

Existing sensor technologies, such as short-wave infrared sensors and X-Ray sensors, can be used to identify and separate a range of materials including plastic polymers, pharmaceutical compounds, and the like. However, there are material identification and classification requirements in some industries that cannot be addressed by the existing sensor technologies.

As an example, plastic sorting in the electronic-waste recycling industry requires a sensing technology that can separate both dark and light colored plastics. One problem in the electronic-waste recycling industry is sorting of black or dark plastics. It is currently estimated that around 10 million tons of electronic-waste plastic is being disposed every year, almost half of it is black plastics.

Current methods of sorting plastic objects (e.g. plastic flakes) have significant drawbacks when trying to identify black and other dark plastics. One method uses short wave infrared (SWIR) cameras to identify the plastic. This technique involves irradiating the unidentified plastic with infrared waves having a wavelength of between about 600-nanometers to about 2500-nanometers. The amount of infrared light transmitted or reflected by the plastic is measured and compared to known polymer spectra in order to identify the type of plastic. However, a problem arises when black and other dark plastics need to be sorted since dark colored plastics absorb infrared radiation and the SWIR cameras cannot detect the dark colored plastics. Instead, the SWIR camera detects a null reading. To date, there is no effective technology solution that satisfactorily addresses the problem of sorting dark plastics in the electronic-waste recycling industry.

In view of the above, there is a need of new systems and methods of identifying, sorting, and separating materials such as light and dark colored plastics and other polymers.

SUMMARY

According to some embodiments, there are provided methods and apparatus for identification and classification of polymers such as plastics and other materials using terahertz sensing techniques. A terahertz wave generated by terahertz sources interacts with materials under test and the transmitted and/or reflected terahertz waves through/off the materials are detected, by terahertz detectors. The detected terahertz waves may contain some unique signatures or "fingerprints" associated with the materials under test, such as their absorption resonance frequencies and physical and/or chemical properties like density, dimensions, refractive index, absorption coefficient, and the like. The materials under test can then be identified and classified based on their properties and unique signatures or fingerprints detected at terahertz frequencies.

In some cases, the detected terahertz waves are analyzed and processed to extract the properties and fingerprints of the materials under test and to compare the results with a database or library to identify the materials under test. The results may be used to send one or more commands to a mechanical sorting device for separating the materials under test, for example, according to their individual responses to the terahertz sensor.

According to some embodiments, there is a terahertz-based material identification system comprising at least one terahertz source for transmitting a terahertz wave for interaction with an object. The interaction results in a resulting terahertz wave that is influenced by the object. The material identification system also comprises at least one terahertz detector for receiving the resulting terahertz wave. The terahertz detector is configured to output measurement data corresponding to the resulting terahertz wave. The material identification system further comprises a processor in communication with the terahertz detector for receiving the measurement data. The processor is configured to calculate an object response signature based on the measurement data, and compare the object response signature to a set of known response signatures so as to identify the object.

The resulting terahertz wave may comprise one of: a transmitted terahertz wave that is transmitted through the object; or a reflected terahertz wave that is reflected from the object or from surroundings around the object.

In some examples, the resulting terahertz wave may be the transmitted terahertz wave, and the terahertz source and the terahertz detector may be configured to operate in transmission mode. In such cases, the terahertz detector is arranged to detect the transmitted terahertz wave.

In some examples, the resulting terahertz wave is the reflected terahertz wave, and the terahertz source and the terahertz detector are configured to operate in reflection mode. In such cases, the terahertz detector is arranged to detect the reflected terahertz wave.

The known response signatures may correspond to a plurality of polymer materials. In some examples, the polymer materials may include at least one dark colored plastic.

The material identification system may further comprise a database for storing the known response signatures.

The processor may be in communication with the terahertz source for operating the terahertz source over a range of terahertz frequencies. Furthermore, the object response signature may be calculated over the range of terahertz frequencies.

In some examples, the terahertz wave may have a frequency of less than about 10-terahertz. More particularly, the terahertz wave may have a frequency of between about 20-GHz and about 4-THz.

The material identification system may further comprise a conveyor for conveying a mixture of objects through the terahertz wave transmitted by the terahertz source.

According to some embodiments, there is a terahertz-based sorting system comprising a conveyor for conveying a mixture of objects, and at least one terahertz source for transmitting a terahertz wave for interaction with at least one of the objects within the mixture. The interaction results in a resulting terahertz wave that is influenced by the object. The sorting system also comprises at least one terahertz detector for receiving the resulting terahertz wave. The terahertz detector is configured to output measurement data corresponding to the resulting terahertz wave. The sorting system further comprises a processor in communication with the terahertz detector for receiving the measurement data. The processor is configured to calculate an object response signature based on the measurement data, and compare the object response signature to a set of known response signatures so as to identify the object. Furthermore, the sorting system comprises a sorting device in communication with the processor for selectively separating the object from the mixture based on the identity of the object.

In some examples, the mixture of objects conveyed by the conveyor may comprise dark colored plastics.

According to some embodiments, there is a method of identifying materials. The method comprises transmitting a terahertz wave for interaction with an object. The interaction results in a resulting terahertz wave that is influenced by the object. The method also comprises receiving the resulting terahertz, wave, generating measurement data based on the resulting terahertz wave received, calculating an object response signature based on the measurement data, and comparing the object response signature to a set of known response signatures so as to identify the object.

The known response signatures may correspond to a plurality of polymer materials. In some examples, the polymer materials may include at least one dark colored plastic.

The terahertz wave may be transmitted over a range of terahertz frequencies and the object response signature may be calculated over the range of terahertz frequencies.

The terahertz wave may have a frequency of less than about 10-terahertz. More particularly, the terahertz wave may have a frequency of between about 20-GHz and about 4-THz.

According to some embodiments, there is a method of sorting materials. The method comprises conveying a mixture of objects, and transmitting a terahertz wave for interaction with at least one of the objects within the mixture. The interaction results in a resulting terahertz wave that is influenced by the object. The method also comprises receiving the resulting terahertz wave, generating measurement data based on the resulting terahertz wave received, calculating an object response signature based on the measurement data, comparing the object response signature to a set of known response signatures so as to identify the object, and selectively separating the object from the mixture based on the identity of the object.

In some examples, the mixture of objects conveyed may comprise dark colored plastics.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of the present specification. In the drawings.

DETAILED DESCRIPTION

Some materials including polymers, plastics, organic and inorganic materials, ceramics, papers and cupboards, and glasses are transparent or semi-transparent to terahertz waves. Furthermore, some of these materials exhibit unique transmission and reflection properties at terahertz frequencies that can be used as a signature or fingerprint for identifying each material. This makes the use of terahertz waves an effective tool to identify and classify these materials based on their properties detected at terahertz frequencies.

Figure 1:
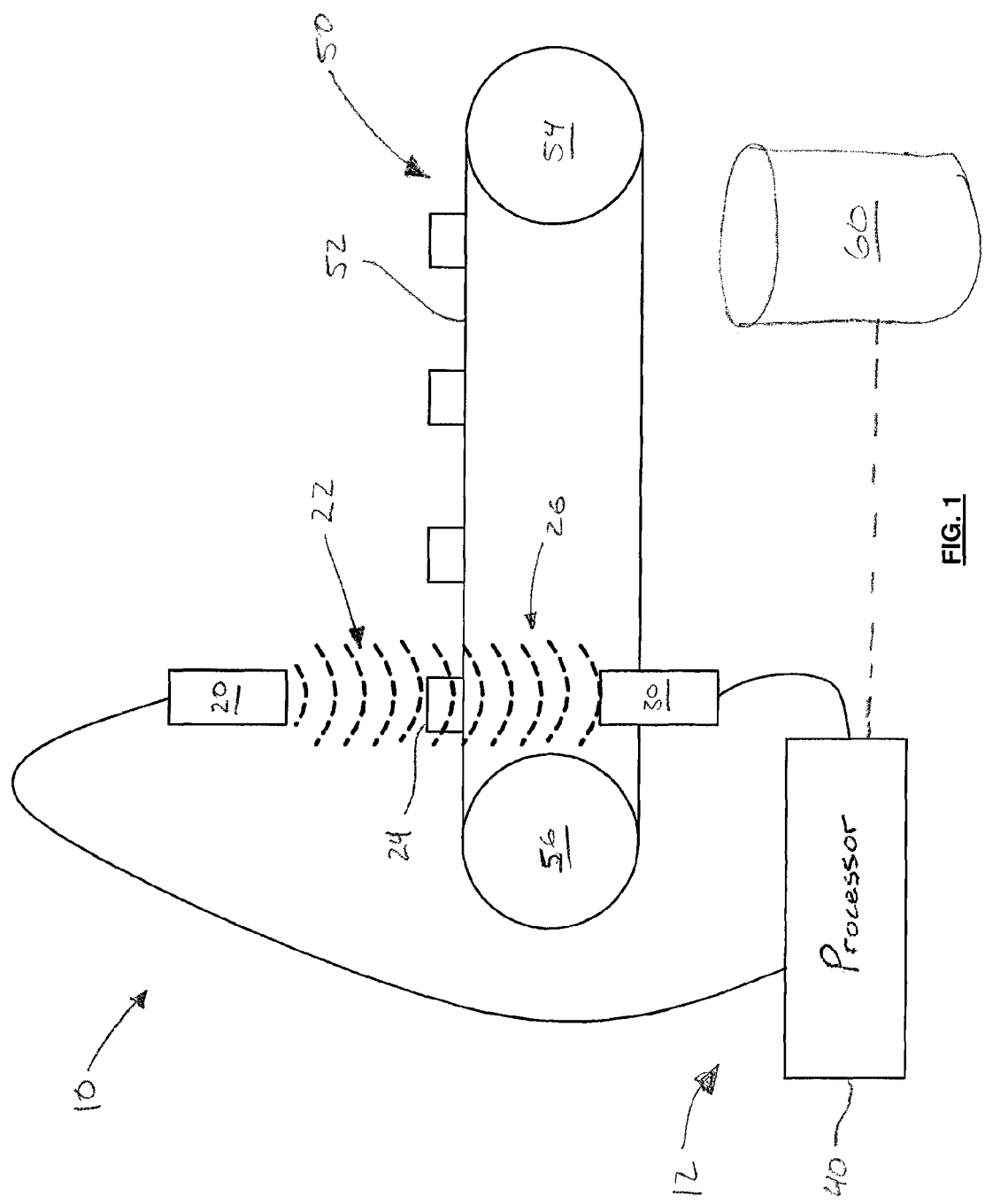
FIG. 1 is a schematic diagram of a terahertz-based material identification system made in accordance with an exemplary embodiment of the present invention, in which the sensor system is operating in transmission mode.

Referring now to FIG. 1 illustrated therein is a schematic diagram of a terahertz-based material identification system 10 made in accordance with an exemplary embodiment of the present invention. The system 10 includes a terahertz sensor assembly 12 comprising a terahertz source 20 (also referred to as a transmitter) for transmitting a terahertz wave 22 toward an object 24 for interaction therewith, and a terahertz detector 30 (also referred to as a receiver) for receiving a resulting terahertz wave 26 after the terahertz wave 22 interacts with the object 24. The terahertz detector 30 outputs measurement data corresponding to the resulting terahertz wave 26.

The terahertz sensor assembly 12 generally operates within the terahertz frequency spectrum. For example, the terahertz wave 22 may have a frequency of less than about 10-THz. More particularly, the frequency may be between about 10-GHz and about 10-THz, or between about 20-GHz and about 4-THz.

The system 10 also includes a processor 40 in communication with the terahertz source 20 and the terahertz detector 30 for controlling the operation thereof. Specifically the processor 40 may control the terahertz source 20 to transmit the terahertz wave at a particular frequency or range of frequencies. Furthermore, the processor 40 is configured to receive the measurement data from the terahertz detector 30 and calculates an object response signature based on the measurement data. Afterwards, the processor 40 compares the object response signature to a database of known response signatures so as to identify the object.

In some embodiments the processor 40 may be a computer, a dedicated microprocessor, a microcontroller, a PLC controller, an electronic circuit, or another type of computing device. In some examples, the processor 40 could be a personal computer running a proprietary program such as a LabView™ program.

As shown in FIG. 1, the material identification system 10 may also include a conveyor 50 for conveying one or more objects through the sensor assembly 12. The conveyor 50 may include a conveyor belt 52 looped around two or more rollers, which may include a driven roller 54 and an idler roller 56.

While not shown, there may also be a sorting device for separating the materials identified by the material identification system 10. For example, the sorting device may include one or more pressurized air nozzles that can be actuated in order to release an air jet that pushes and diverts certain identified materials away from the mixture of objects (e.g. to a separate container or hopper). The sorting device could also include mechanical arms, secondary conveyors, drop chutes, and the like.

The system 10 may also include a database 60 for storing one or more known response signatures. The known response signatures may be compiled by individually testing known materials and recording the object response signature associated with each particular material. In some embodiments, the database 60 may be pre-loaded with a number of known response signatures for particular compounds such as dark colored plastics and other polymer materials. In some embodiments, the processor 40 may be configured to add or update the database 60 with new entries of known response signatures.

In use, a mixture of materials to be identified and sorted (also referred to as samples or objects) move along the conveyor belt 52 and pass in front of the terahertz source 20. The terahertz wave 22 interacts with the sample. The interaction results in resulting terahertz wave 26, which is subsequently received and detected by the terahertz detector 30.

As shown, the detector 30 is located on the other side of the object 24 and the conveyor belt 52 as the terahertz source 20. Accordingly, the terahertz wave 22 is generally transmitted through the object 24, and the resulting terahertz wave 26 is a transmitted terahertz wave. In other words, the transmitted terahertz wave that is received by the terahertz detector 30 is a transmitted portion of the terahertz wave 22. This configuration of the terahertz sensor assembly 12 may be generally referred to as transmission mode.

The measured terahertz waves are processed to extract one or more physical or chemical properties of the materials such as refractive index, absorption coefficient, absorption signature, thickness, dimensions, and the like. The resulting properties may be used to calculate an object response signature, which can then be compared against a database or library of known response signatures to identify and classify the materials under test.

In some examples, the terahertz wave 22 transmitted by the terahertz source 20 can be a narrow band terahertz signal, for example, generated by a terahertz photo-mixer, a terahertz transistor, a backward wave oscillator, a quantum cascade laser, or any other narrow band terahertz sources. In other examples, the terahertz wave 22 transmitted by the terahertz source 20 can be a wide band terahertz pulse, for example, generated by a terahertz photoconductive antenna or any other wide band terahertz sources.

The terahertz detector 30 generally receives the resulting terahertz wave 26, which may be a transmitted portion of the terahertz wave 22. In some examples, the terahertz detector 30 may be a photoconductive receiver, an electro-optical receiver, or another type of terahertz receiver. The terahertz detector 30 could also be a terahertz camera having a field of view selected to record one or more terahertz waves passing through the materials under test.

In some cases, reference measurement data may be recorded when there is no material under test at the path of the terahertz wave. This can be used to further process the measurement data as will be described later below.

Figure 2:
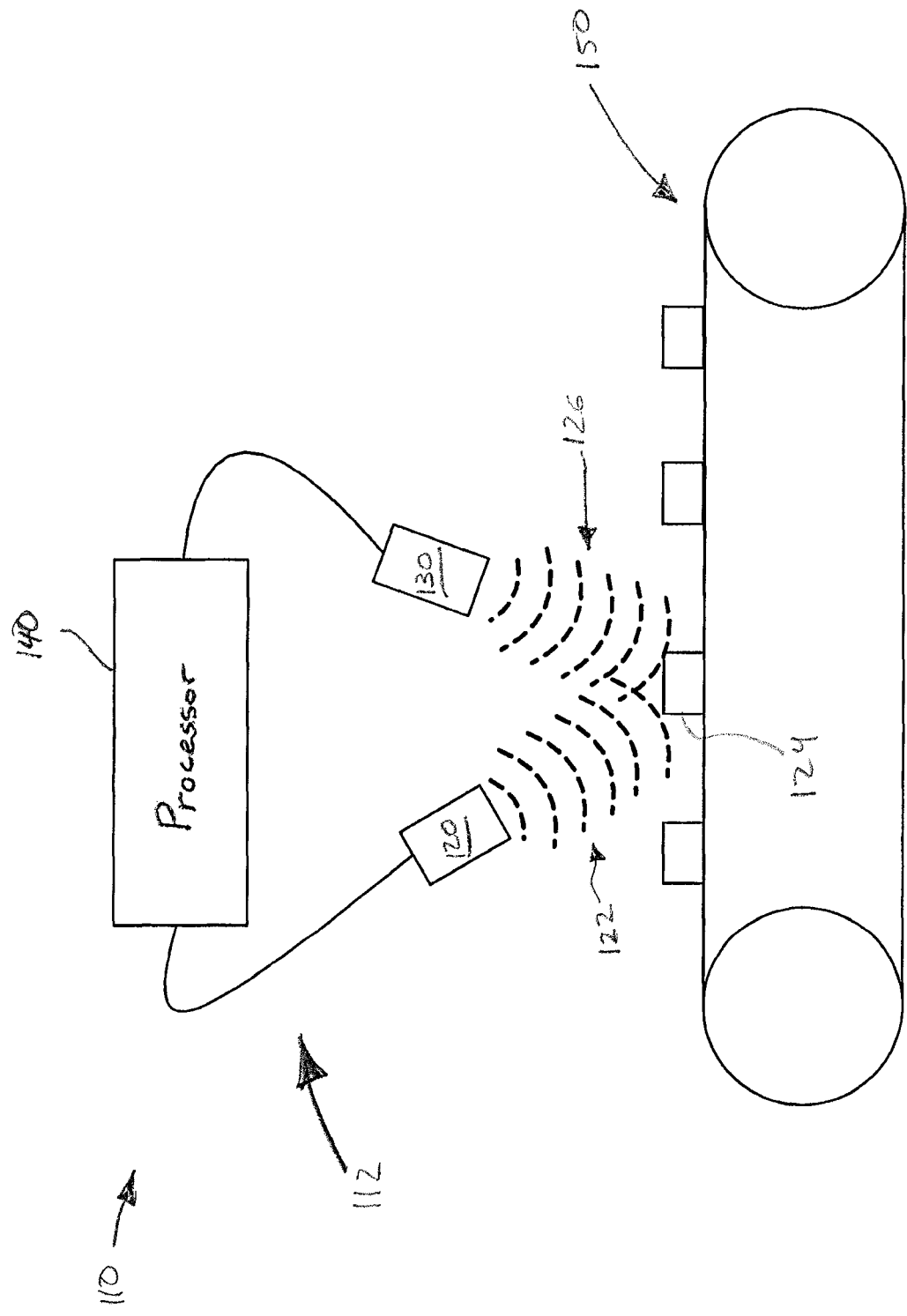
FIG. 2 is a schematic diagram of a terahertz-based material identification system operating in reflection mode so that a terahertz beam reflects off an outer surface of a material sample passing thereunder.

Referring now to FIG. 2 illustrated therein is a schematic diagram of a material identification system 110 made in accordance with another exemplary embodiment of the present invention. The material identification system 110 is similar in some respects to the material identification system 10 and where appropriate similar elements are given similar reference numerals incremented by one hundred. For example, the system 110 includes a terahertz sensor assembly 112 comprising a terahertz source 120 and a terahertz detector 130, a processor 140, and a conveyor 150.

One difference is that the terahertz sensor assembly 112 is configured to operate in reflection mode. Specifically, the terahertz detector 130 is located on the same side of the object 124 and the conveyor 150 as the terahertz source 120.

Accordingly, the terahertz wave 122 is generally reflected off the object 124 or other surroundings around the object 124, and the resulting terahertz wave 26 is a reflected terahertz wave. In other words, the reflected terahertz wave that is received by the terahertz detector 130 is a reflected portion of the terahertz wave 122.

Figure 3:
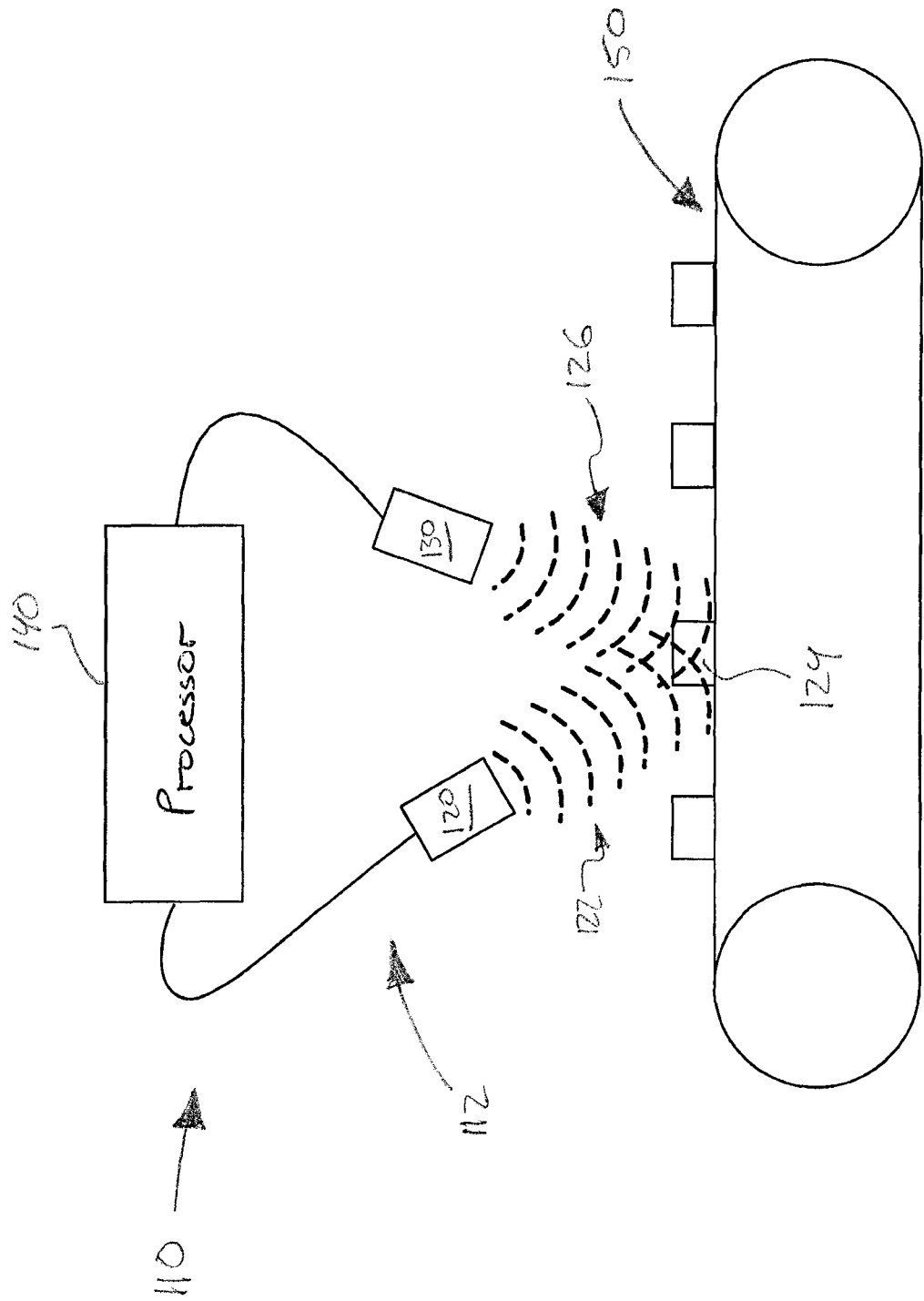
FIG. 3 is a schematic diagram of a terahertz-based material identification system operating in reflection mode so that a terahertz beam penetrates through a material sample passing thereunder and reflects off a conveyor belt.

Referring now to FIG. 3, the sensor assembly 112 may also be configured to transmit terahertz waves 122 that penetrate through the object 124 and reflect off the conveyor 150 (or other surroundings around the object 124) back towards the terahertz detector 130. In this configuration, the terahertz wave 122 interacts with the bulk of the material under test (i.e. the object 124), and not just the surface thereof as with the embodiment shown in FIG. 2. This can improve accuracy of the measurement data and classification. For example, it may allow an absorption coefficient to be measured over the entire thickness of the sample.

Figure 4:
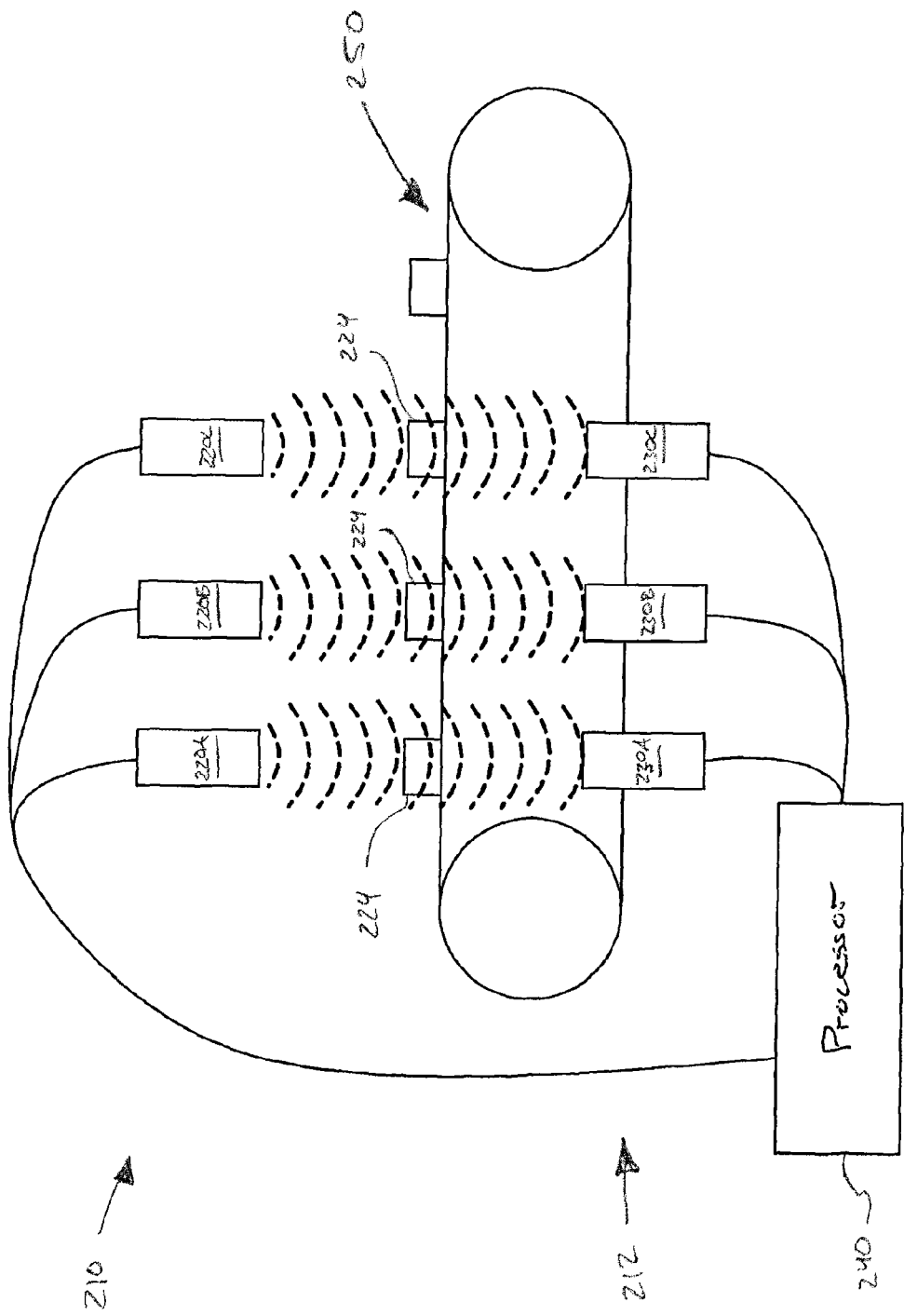
FIG. 4 is a schematic diagram of a terahertz-based material identification system that includes multiple sensor heads, in which the sensor system is operating in transmission mode.

Referring now to FIG. 4 illustrated therein is schematic diagram of another material identification system 210 made in accordance with another exemplary embodiment of the present invention. The material identification system 210 is similar in some respects to the material identification system 10 and where appropriate similar elements are given similar reference numerals incremented by two hundred. For example, the system 210 includes a terahertz sensor assembly 212, a processor 240, and a conveyor 250.

One difference is that the terahertz sensor assembly 212 includes a plurality of terahertz sources 220A, 220B, and 220C and a plurality of terahertz detectors 230A, 230B, and 230C in communication with the processor 240. Specifically, there are three terahertz sources and three terahertz detectors. In other embodiments, there may be a greater or lesser number of sources and detectors.

The terahertz sources and detectors can be arranged in series and/or in parallel to identify and classify objects 224 or materials under test passing through terahertz waves. For example, in the illustrated embodiment, the sensors and detectors are arranged in series so that each terahertz source is paired with a respective terahertz detector. Thus, a terahertz wave transmitted from a particular source is received by the corresponding detector. This allows multistage identification and sorting of materials (e.g. to progressively identify and separate certain materials from the mixture of objects). Alternatively, the sensor and detector pairings may be arranged in parallel. This may allow identification of materials and objects that are spread out along the width of the conveyor 250.

In some examples, the terahertz sources 220A, 220B, and 220C may be in the form of an array of individual transmitter modules with separate housing/packaging units, or alternatively, the terahertz sources 220A, 220B, and 220C can be in the form of an array of transmitters in a single housing/packaging unit.

The terahertz detectors 230A, 230B, and 230C can also be in the form of an array of individual receiver modules with separate housing/packaging units, or alternatively, the terahertz detectors 230A, 230B, and 230C can be in the form of an array of receivers all in a single housing/packaging unit.

Figure 5:
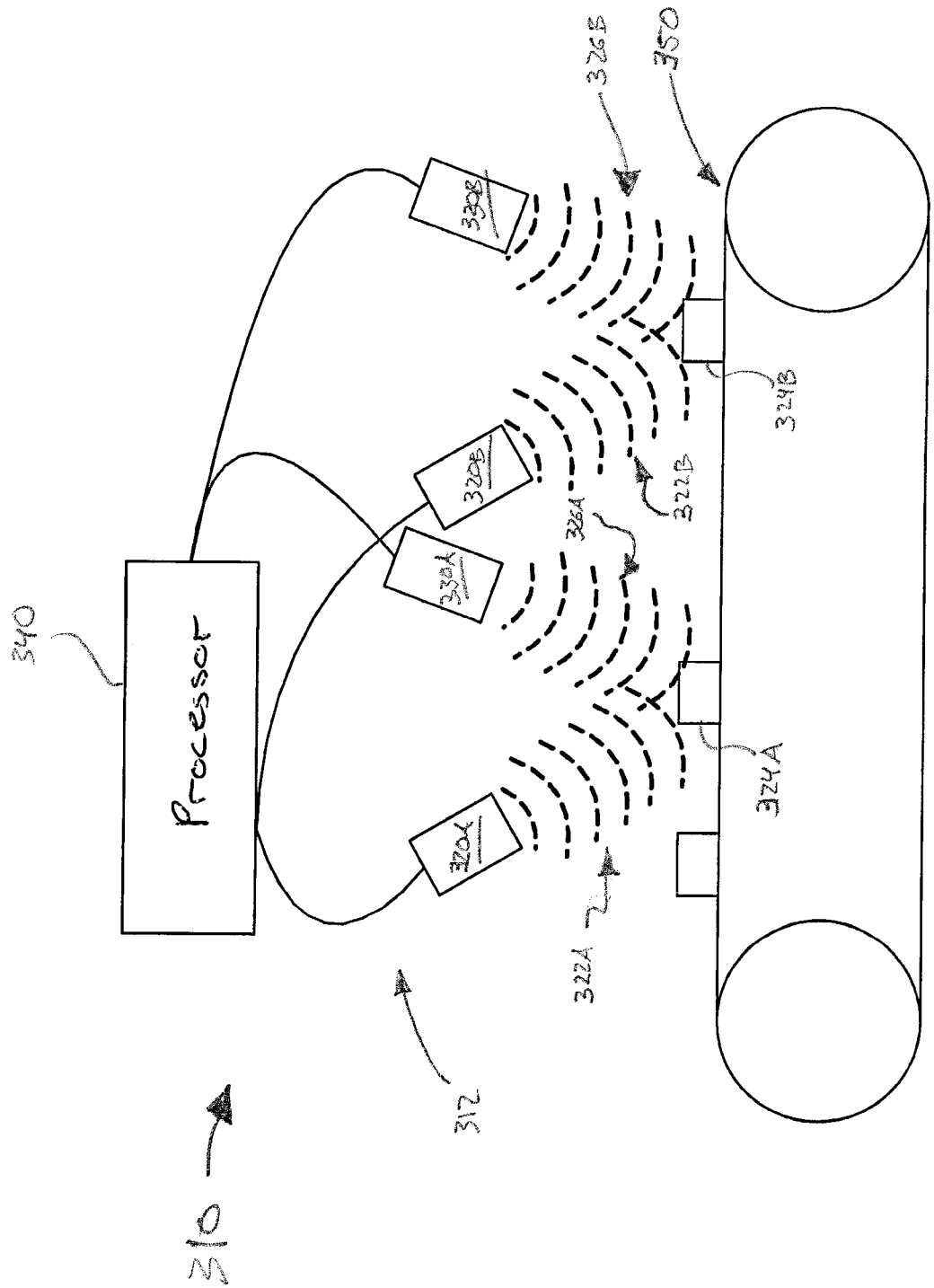
FIG. 5 is a schematic diagram of a terahertz-based material identification system that includes multiple sensor heads, in which the sensor system is operating in reflection mode so that a terahertz beam reflects off an outer surface of a material sample passing thereunder.

Referring now to FIG. 5 illustrated therein is schematic diagram of another material identification system 310 made in accordance with another exemplary embodiment of the present invention. The material identification system 310 is similar in some respects to the material identification system 210 and where appropriate similar elements are given similar reference numerals incremented by one hundred. For example, the system 310 includes a terahertz sensor assembly 312 comprising a plurality of terahertz sources 320A, 320B and a plurality of terahertz detectors 330A, 330B, a processor 340, and a conveyor 350.

One difference is that the terahertz sensor assembly 312 is configured to operate in reflection mode, similar to the embodiment shown in FIG. 2. Specifically, each terahertz detector 330A, 330B is located on the same side of the object 324 and the conveyor 350 as the respective terahertz source 320A, 320B. Thus, terahertz waves 322A, 322B impinging objects 324A, 324B interact with the objects 324A, 324B. The interaction results in resulting terahertz waves 326A, 326B that reflect off surfaces of the objects 324A, 324B and are subsequently received by the respective terahertz detectors 330A, 330B. In other words, the resulting terahertz waves 326A, 326B are reflected terahertz waves that are reflected portions of the terahertz waves 322A, 322B.

In some embodiments, the terahertz detectors 330A, 330B may include a terahertz camera with a field of view selected to record the terahertz waves reflecting off the materials under test.

Figure 6:
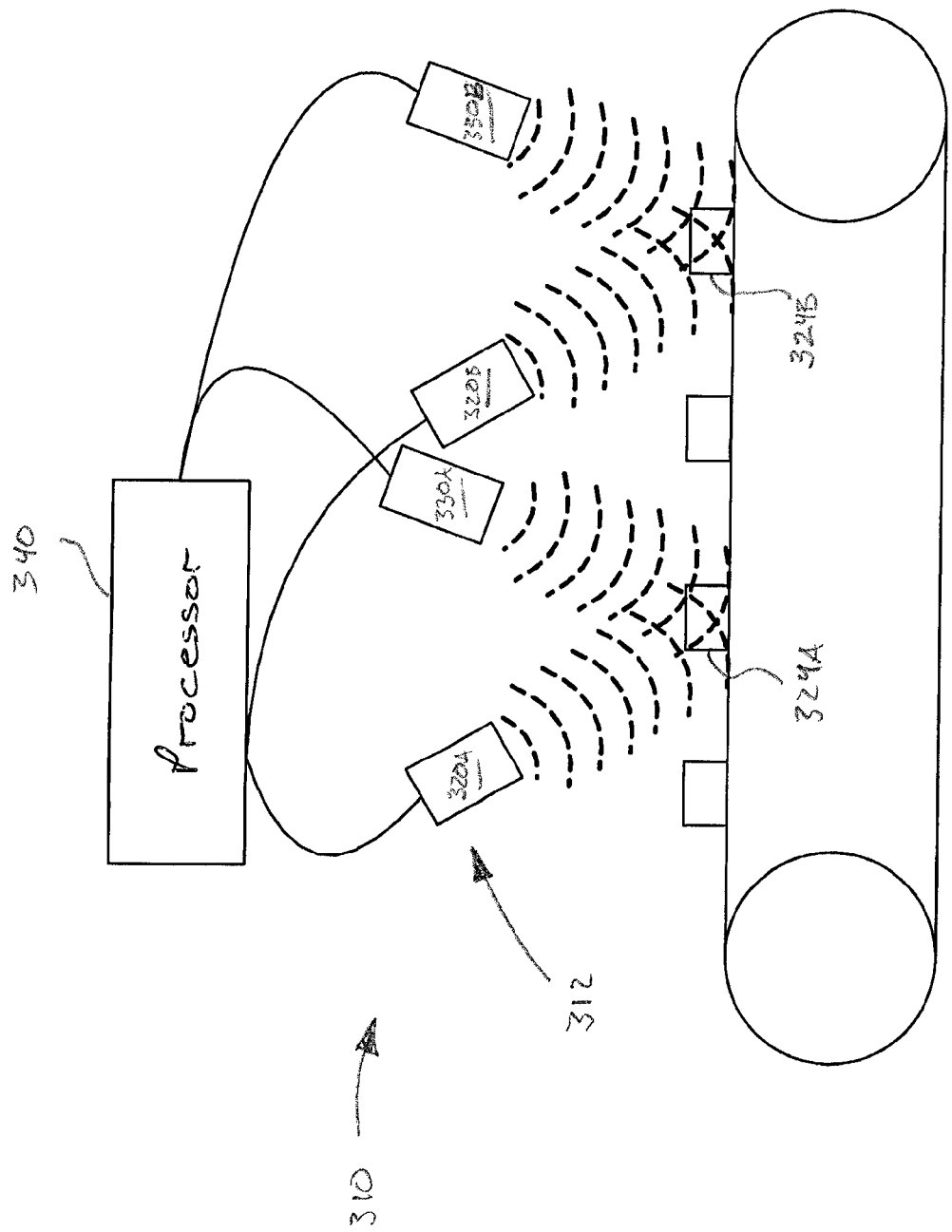
FIG. 6 is a schematic diagram of a terahertz-based material identification system that includes multiple sensor heads, in which the sensor system is operating in reflection mode so that a terahertz beam penetrates through a material sample passing thereunder and reflects off a conveyor belt.
Figure 7A:
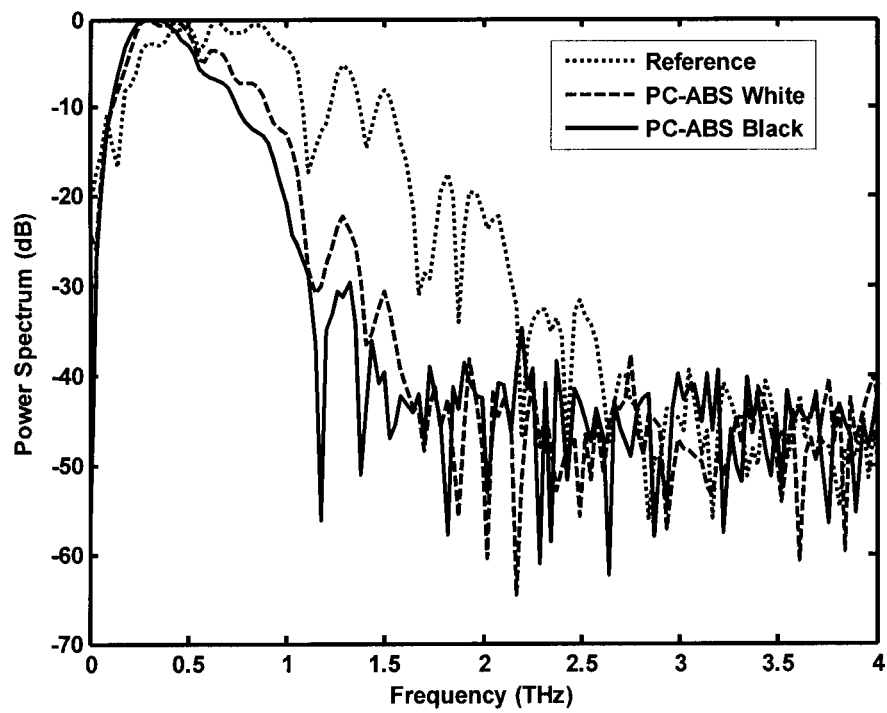
FIGS. 7(a)-(e) are, graphs showing exemplary measurement data for plastic samples tested using a terahertz-based material identification system made in accordance with an embodiment of the present invention.
Figure 7B:
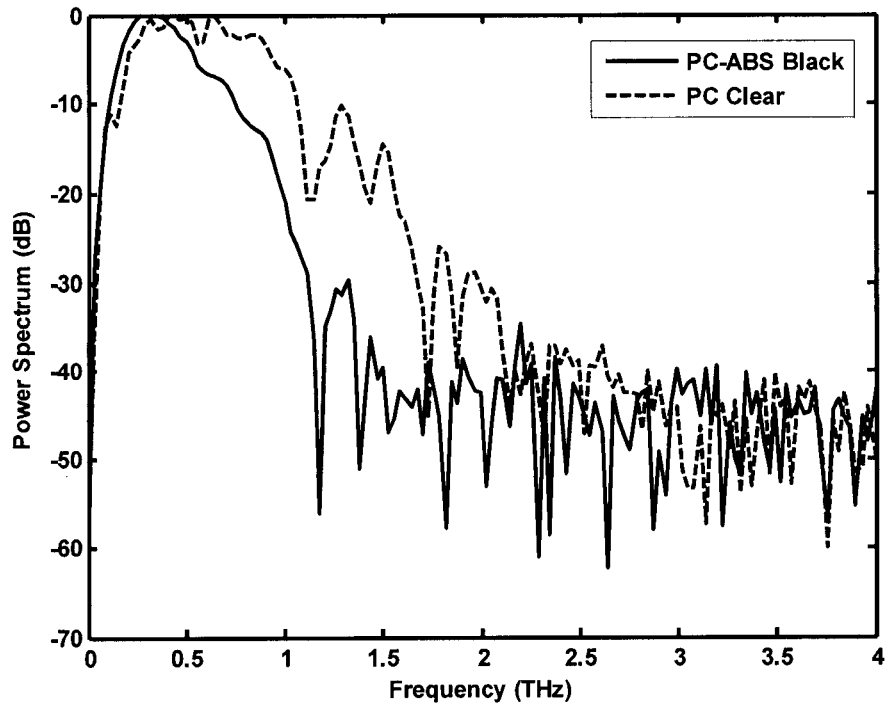
Figure 7C:
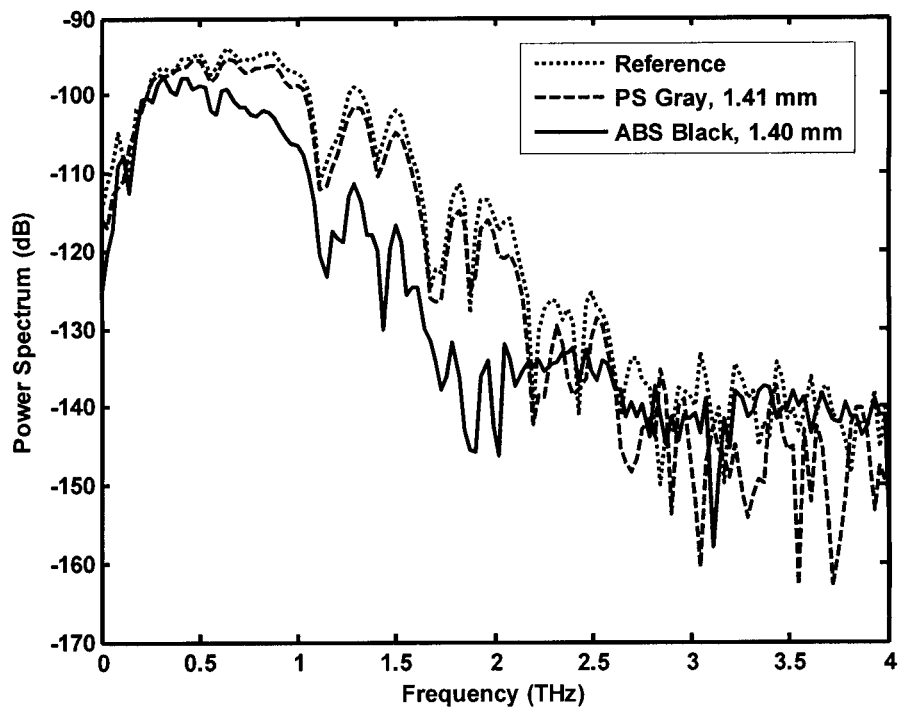
Figure 7D:
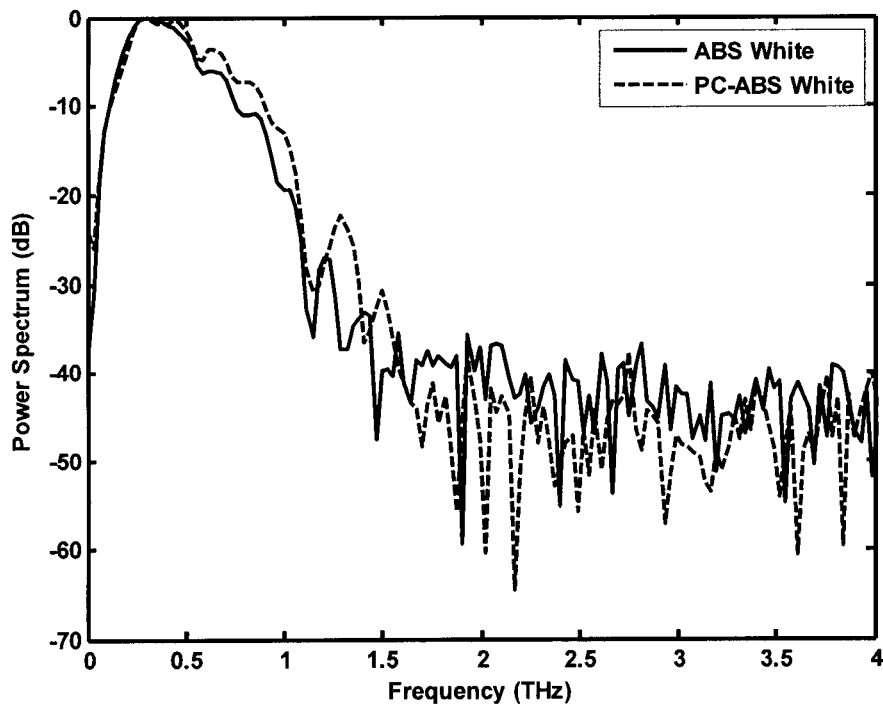
Figure 7E:
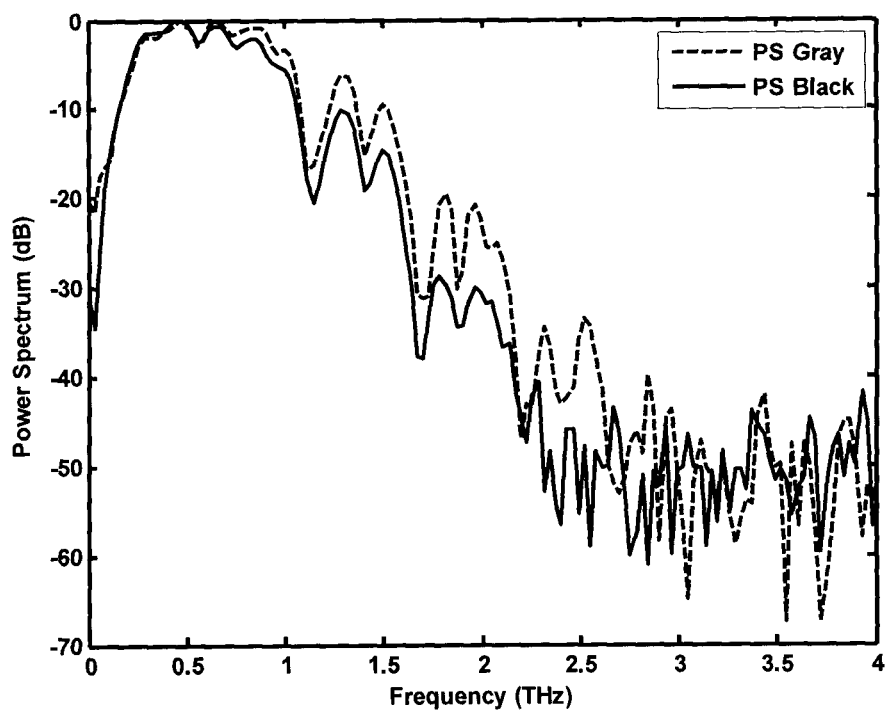

Referring now to FIG. 6, the sensor assembly 312 may also be configured to transmit terahertz waves that penetrate through the objects 324A, 324B and reflect off the conveyor 350 (or other surroundings around the objects 324A, 324B) back towards the terahertz detectors 330A, 330B, as similar to the embodiment shown in FIG. 3.

Referring now to FIGS. 7(a)-7(e) illustrated therein are measurement results collected from a terahertz-based material identification system made in accordance with an embodiment of the present invention. The measurement results correspond to a set of plastic samples, some of which may be produced in the electronic-waste recycling industry. The plastic samples include white polycarbonate acrylonitrile butadiene styrene (PC-ABS White), black polycarbonate acrylonitrile butadiene styrene (PC-ABS Black), clear polycarbonate (PC Clear), gray polystyrene (PS Gray), black acrylonitrile butadiene styrene (ABS Black), white acrylonitrile butadiene styrene (ABS White), and black polystyrene (PS Black).

For each sample, terahertz waves were transmitted from a terahertz source over a range of frequencies, namely from about 0-THz to about 4-THz. A portion of each terahertz wave was detected by a terahertz detector and measurement data was recorded by a processor. The graphs in FIGS. 7(a)-7(e) show the power spectrums for each sample, and in some cases along with a reference measurement without having a sample located between the source and detector.

As shown, the terahertz power spectrum responses of plastic samples are distinguishable, even for black and other dark colored plastics, making it possible to separate and classify plastic samples under test using the terahertz-based material identification system. Each frequency point on the recorded spectrum can be used to identify and classify a particular plastic sample in a mixture. For example, if the measure point is near a particular known data point for a material, it may indicate that the measured sample corresponds to the known sample (e.g. representing a figure of merit). In some examples, the response over the entire spectrum can be used as a unique signature or fingerprint to identify and classify the materials with greater accuracy than using single data points.

Figure 8A:
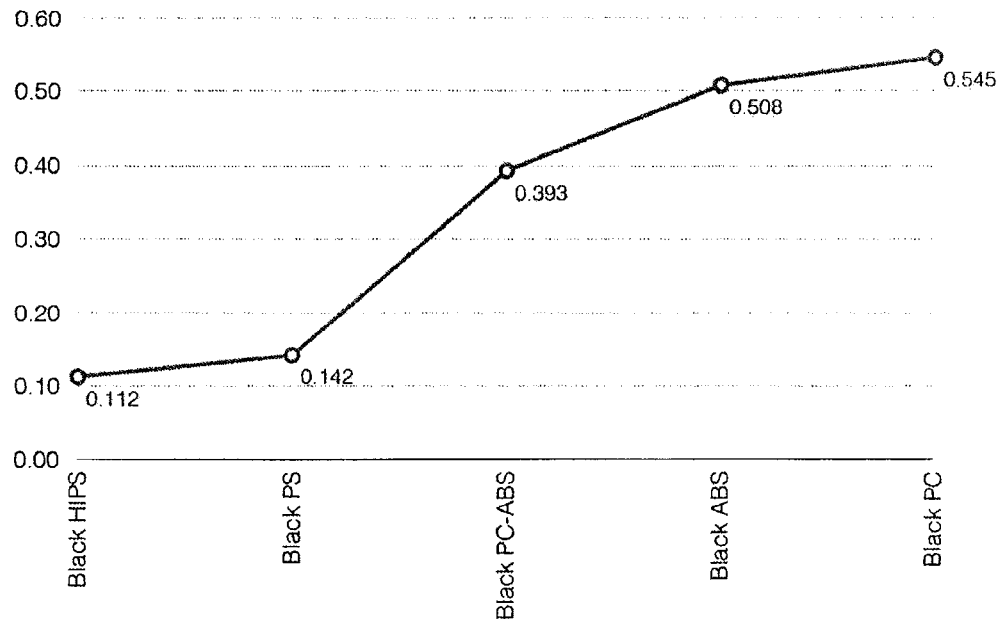
FIG. 8(a)-8(c) are graphs showing absorption coefficients calculated from measurement data for plastic samples tested using a terahertz-based material identification system made in accordance with an embodiment of the present invention.
Figure 8B:
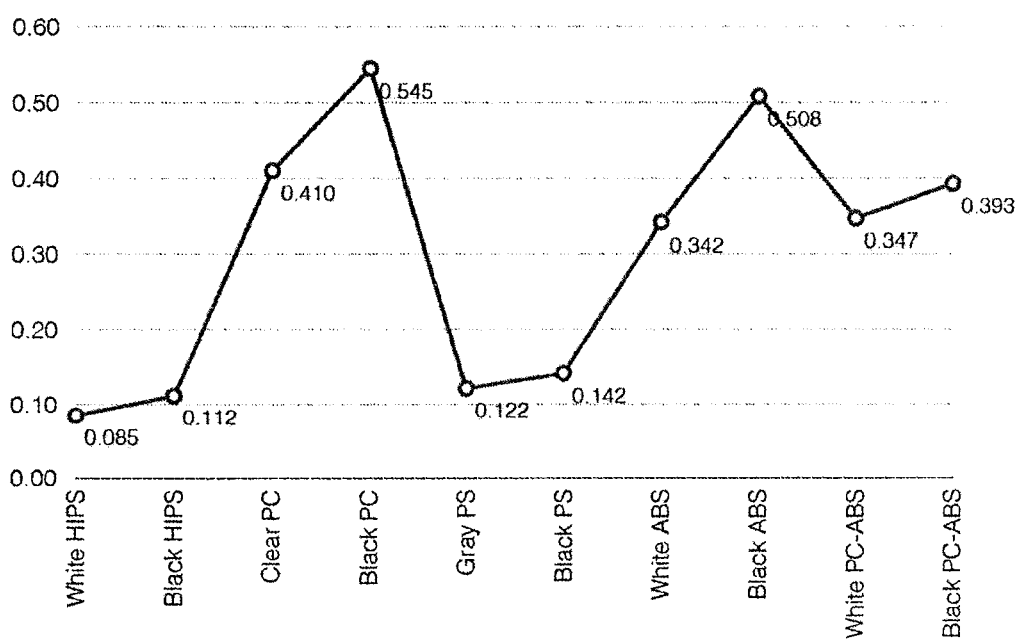
Figure 8C:
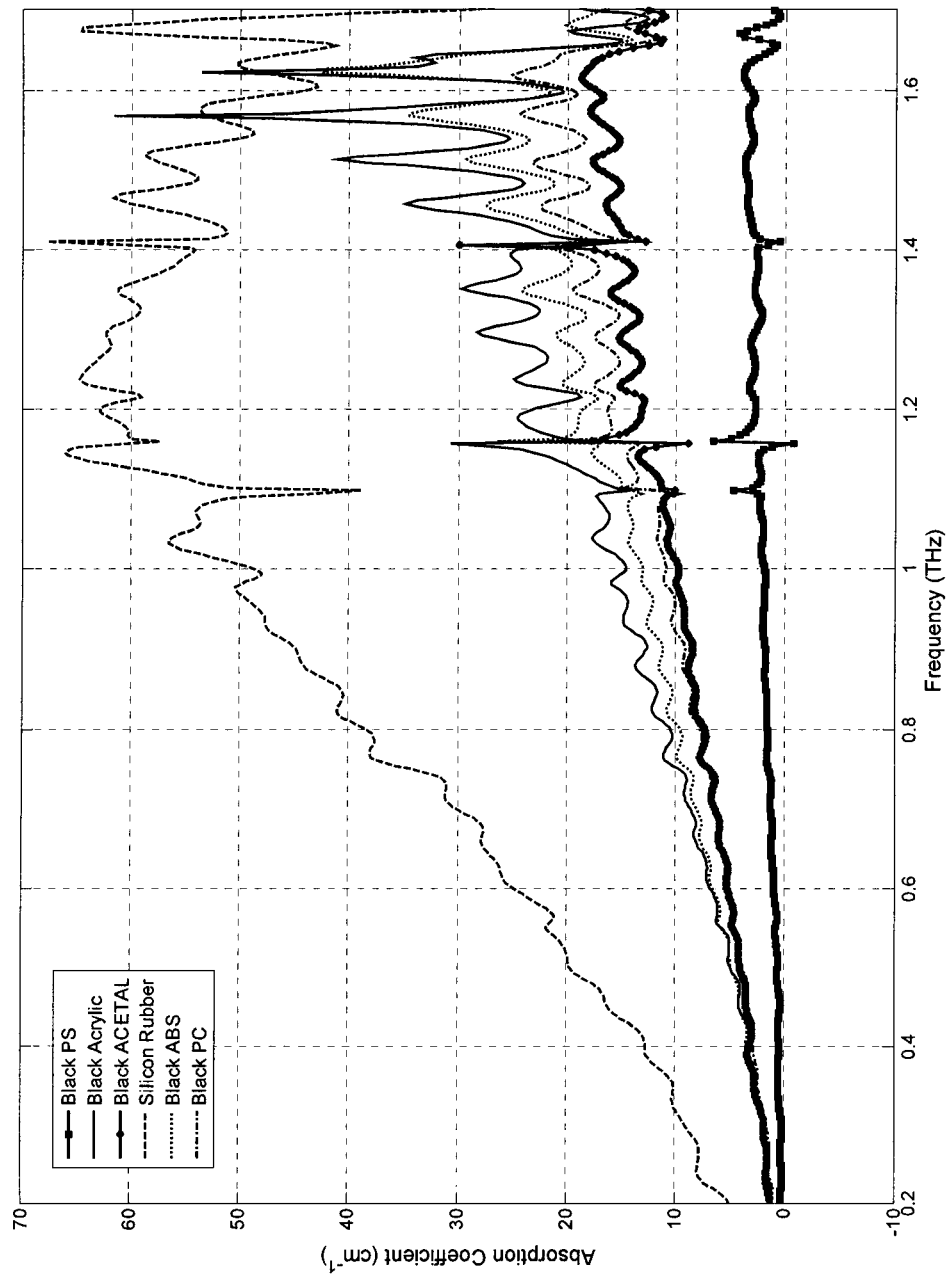

Referring now to FIGS. 8(a)-8(c) illustrated therein are graphs showing absorption coefficients at terahertz frequencies for a set of plastic samples produced in electronic-waste recycling industry including white high-impact polystyrene (White HIPS), black high-impact polystyrene (Black HIPS), clear polycarbonate (Clear PC), black polycarbonate (Black PC), gray polystyrene (Gray PS), black polystyrene (Black PS), white acrylonitrile butadiene styrene (White ABS), black acrylonitrile butadiene styrene (Black ABS), white polycarbonate acrylonitrile butadiene styrene (White PC-ABS), black polycarbonate acrylonitrile butadiene styrene (Black PC-ABS), black polystyrene (Black PS), black acrylic, black ACETAL, and silicon rubber.

Each data point on the graphs shown in FIGS. 8(a) and 8(b) represents the absorption coefficient of a material sample tested at terahertz frequencies. More specifically, the absorption coefficients were calculated by measuring the time-averaged intensity of terahertz pulses received by the terahertz detector, and comparing the measured value to the initial intensity of each pulse. Each terahertz pulse included a spectrum of terahertz frequencies from about 0-THz to about 4-THz. The calculated absorption coefficients can be stored in a database and can be subsequently compared with absorption coefficients for unknown materials being tested in order to identify and separate different materials.

The absorption coefficients can be calculated using a terahertz-based material identification system made in accordance with an embodiment of the present invention. For example, one or more of the processors 40, 140, 240, 340, described above may be configured or programmed to calculate the absorption coefficients based on the following methodology.

In operation, when a terahertz wave passes through a material such as a piece of plastic, its amplitude exponentially reduces with an exponential coefficient called the absorption coefficient "α" given by the following formula:

$$E_t = E_i e^{-\alpha d},$$

where "$E_i$" is the initial amplitude of the electromagnetic field, "d" is the sample thickness, and "$E_t$" is the amplitude of the electromagnetic field at that thickness. By measuring the terahertz electric field with, and without the sample, and knowing sample thickness, d, the processor 40 can be configured or programmed to calculate the absorption coefficient using the following formula:

$$\alpha = \frac{1}{d} \ln \frac{E_i}{E_t}$$

The absorption coefficient is a parameter independent of the sample thickness, and represents the absorption characteristics of the material that the sample is made of.

It is possible to calculate the sample thickness "d". Specifically, a terahertz wave passing through a sample having a thickness "d" and refractive index "n" experiences a delay of "Δt" compared to a wave with no sample between the source and detector. The delay "Δt" is related to the thickness "d" and the refractive index "n" by the following formula:

$$\Delta t = \frac{d(n-1)}{c}$$

where "c" is the speed of light in the surrounding medium (e.g. the speed of light in air). By measuring the time delay Δt and knowing the refractive index of the sample under test, the processor 40 can be configured or programmed to calculate the thickness of the sample using the above formula. In some cases, the refractive index may be known or estimated. For example, a number of plastics have a refractive index of about 1.6 and this value can be used as an estimate. The refractive index could also be measured directly using one or more known measurement techniques.

In some examples, the absorption coefficients may be calculated at specific terahertz frequencies in the frequency domain. For example, as shown in FIG. 8(c), the frequency-dependent absorption coefficient is shown over a range of frequencies from 0.2-THz to about 1.7-THz. Using the frequency-dependent absorption coefficient to identify materials can be more accurate than using the time-averaged absorption coefficients shown in FIGS. 8(a) and 8(b). However, the time-averaged absorption coefficients can be calculated easier and faster.

Figure 9:
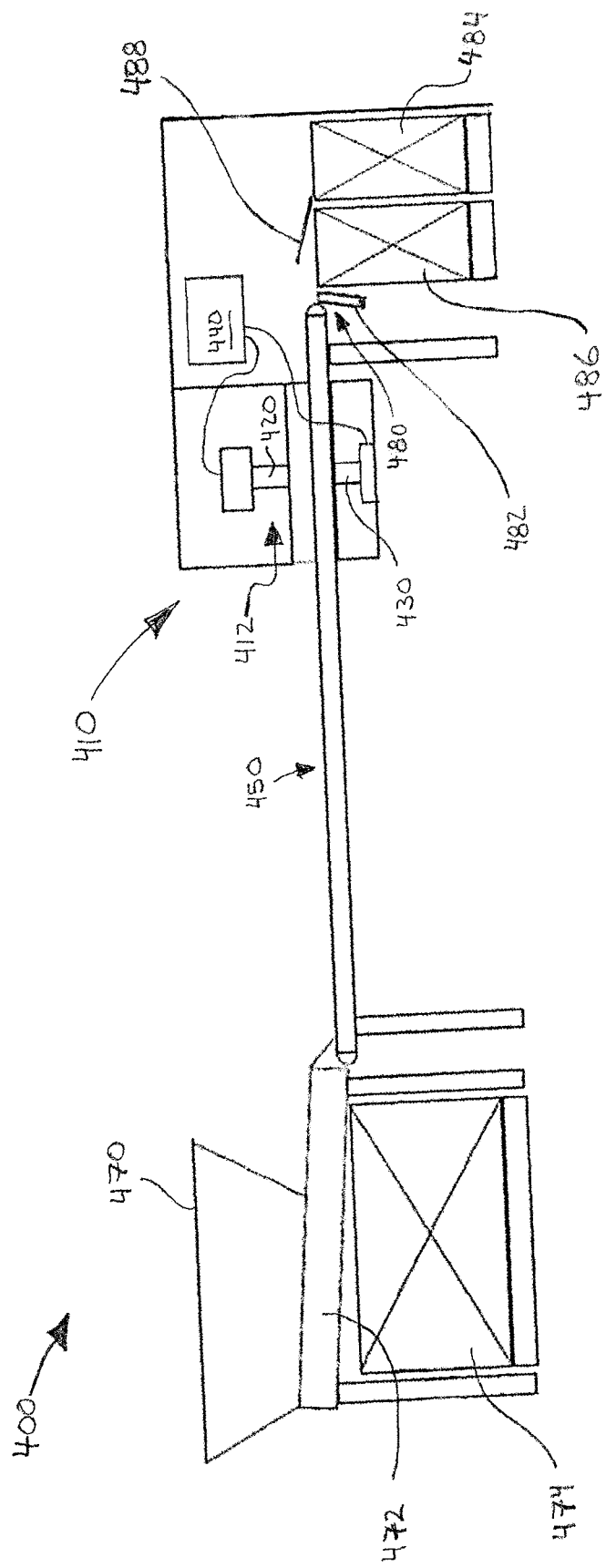
FIG. 9 is a schematic diagram of a material sorting system made in accordance with another embodiment of the present invention.

Referring now to FIG. 9, illustrated therein is schematic diagram of a terahertz-based sorting system 400 made in accordance with another exemplary embodiment of the present invention. The sorting system 400 includes a terahertz-based material identification system 410, which is similar in some respects to the material identification system 10 and where appropriate similar elements are given similar reference numerals incremented by four hundred. For example, the material identification system 410 includes a terahertz sensor assembly 412 comprising a terahertz source 420 and a terahertz detector 430, a processor 440, and a conveyor 450.

The sorting system 400 also includes a source of objects or materials, such as an input hopper 470, for supplying a mixture of objects to the conveyor 450. The mixture may include dark-colored plastics and other polymer materials. The conveyor 450 then conveys the mixture of objects towards the sensor assembly 412 where one or more objects are identified based on the measurement data collected by the terahertz detector 430.

In some examples, the input hopper 470 may supply the mixture of objects onto the conveyor 450 in a mono-layer. This may allow more accurate identification of each piece of material passing through the sensor assembly 412.

Furthermore, the conveyor 450 may have a width of about 1-foot and may have a speed of about 3 m/s. In other examples, the conveyor width smaller or larger, and the conveyor speed may be faster or slower.

The sorting system 400 may also include a vibratory screen 472 and a collection bin 474 adjacent to the input hopper 470. The vibratory screen may initially receive the mixture of objects and remove small objects that cannot be readily identified using the terahertz sensor assembly 412. In other examples, there may be another type of pre-sorting device for initially removing some objects from the mixture. For example, a magnetic separator may be used to remove some metals.

Downstream of the terahertz sensor assembly 412, the sorting system 400 includes a post-identification sorting device 480 in communication with the processor 440 for selectively separating objects from the mixture based on the identity of the object determined by the material identification system 410. For example, as shown, the sorting device 480 may include one or more pressurized air nozzles 482 for selectively discharging an air jet towards an object in order to redirect and separate that object from the mixture. More specifically, the air jet may push and lift a selected object off the conveyor 450 and direct or divert the selected object toward a first output hopper 484, while the remainder of the mixture is conveyed into a second output hopper 486.

A baffle 488 may be used to help direct the selected object into the first output hopper 484. More specifically, the baffle 488 may be placed over the second output hopper 486 and may be sloped downward toward the first output hopper 484.

In other examples, the sorting device 480 could have other configurations, such as a mechanical arm, a secondary conveyor, a drop chute, and the like.

Figure 10:
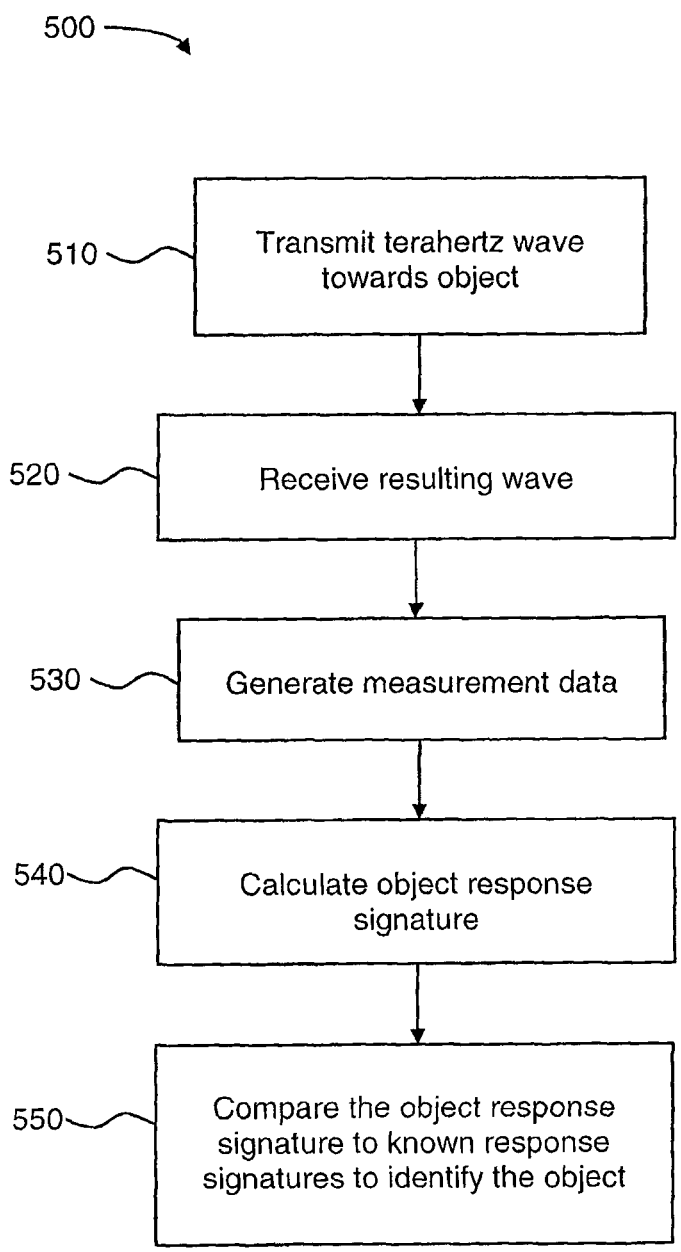
FIG. 10 is a flow chart illustrating a method of identifying materials according to another embodiment of the present invention.

Referring now to FIG. 10, illustrated therein is a method 500 of identifying materials using terahertz waves according to another embodiment of the present invention. The method 500 includes steps 510, 520, 530, 540 and 550.

Step 510 includes transmitting a terahertz wave towards an object for interaction therewith. For example, the terahertz wave may be transmitted from one of the terahertz sources described above. The terahertz wave generally interacts with the object and results in a resulting terahertz wave, which may be a transmitted terahertz wave or a reflected terahertz wave.

Step 520 includes receiving the resulting terahertz wave. For example, the resulting terahertz wave may be received or detected by one of the terahertz detectors described above.

In some examples, the method 500 may be performed in a way that allows for operation in a transmission mode such that the resulting terahertz wave is a transmitted portion of the terahertz wave (e.g. such as with the systems shown in FIGS. 1 and 4). In other examples, method 500 may be performed in a way that allows for operation in a reflection mode such that the resulting terahertz wave is a reflected portion of the terahertz wave (e.g. such as with the systems shown in FIGS. 2-3 and 5-6).

Step 530 includes generating measurement data based on the resulting terahertz wave received. For example, the measurement data may be generated by one of the terahertz detectors described above.

Step 540 includes calculating an object response signature based on the measurement data. For example, the object response signature may be calculated using a processor programed to use one or more of the formulas and methodologies described above.

Step 550 includes comparing the object response signature to a set of known response signatures so as to identify the object. For example, a processor may compare the calculated response signature to one or more known response signatures stored in a database such as the database 60.

In some examples, the terahertz wave may be transmitted over a range of terahertz frequencies, and the object response signature may be calculated over the range of terahertz frequencies. This may help to provide more accurate identification of materials.

Figure 11:
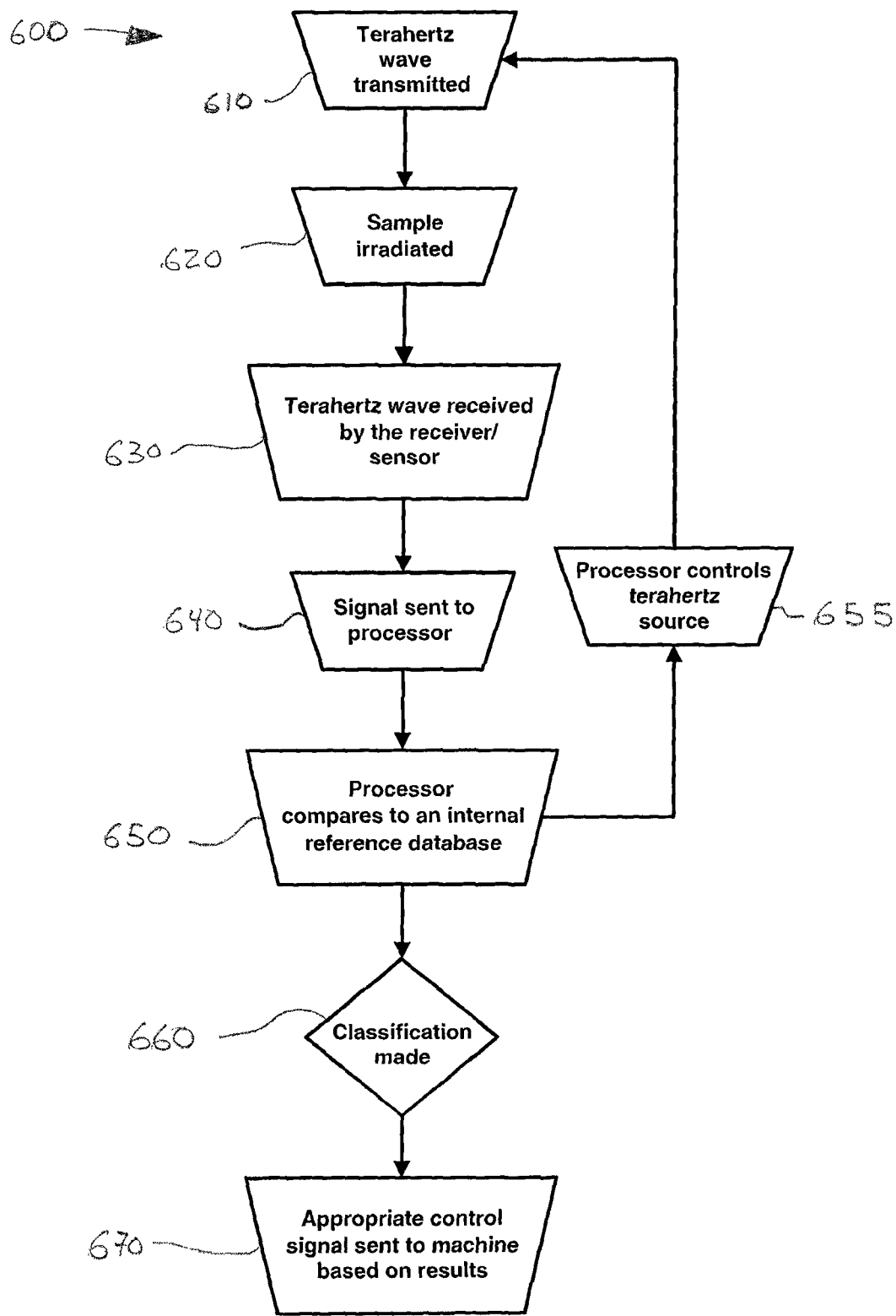
FIG. 11 is a flow chart illustrating a method of measuring, classifying, and sorting materials such as plastic samples according to another embodiment of the present invention.

Referring now to FIG. 11, illustrated therein is a method 600 of sorting materials using terahertz waves according to another embodiment of the present invention. The method 600 includes steps 610, 620, 630, 640, 650, 660, and 670.

Step 610 includes transmitting a terahertz wave, for example, using one of the terahertz sources described above.

Step 620 includes irradiating a sample or object with the terahertz wave. For example, the terahertz wave may interact with the object and result in a resulting terahertz wave. The resulting terahertz wave may be a transmitted or reflected portion of the terahertz wave.

Step 630 includes receiving the resulting terahertz wave. For example, the resulting terahertz wave may be received or detected by one of the terahertz detectors described above.

Step 640 includes sending a signal or other measurement data to a processor such as a central processing unit (CPU).

Step 650 includes comparing the measurement data to known response signatures, which may be stored in and internal reference database. Prior to completing the comparison, the measurement data may be processed to calculate an object response signature that is in a similar format as the known response signatures.

Step 660 includes making a material classification based on the comparison performed at step 650. For example, step 660 may identify the particular material or the type of material being tested.

Step 670 includes selectively outputting a control signal to a sorting device or machine for separating the tested sample from the mixture of objects. For example, the control signal may be sent to the air nozzles 482 or another type of sorting device.

After step 650, the method 600 may repeat steps 610-650. For example, as shown at step 655, a processor or CPU may control the terahertz source or otherwise generate one or more additional terahertz waves to provide further measurement data prior to making the classification at step 660. In some examples, the additional terahertz waves may be the same as the previous terahertz waves. Recording two or more measurements for each sample may enhance the accuracy of the measurement data. In some examples, the additional terahertz waves could be different from the previous terahertz waves. This may help to provide more data for classifying the material being tested. For example, step 655 may be carried out so that the terahertz waves are transmitted over a range of frequencies, and multiple comparisons are completed at step 650 over the range of frequencies.

Generally, one or more methods and apparatus described herein may be used to identify or sort materials such as plastic materials. More particularly, the use of terahertz waves can be useful in identifying and sorting black and other dark plastics found in the electronic waste recycling industry because the terahertz waves tend to interact with these dark plastics and result in resulting terahertz waves that can be detected. For example, it is possible to detect reflected or transmitted portions of the terahertz waves, which can then be used as a signature or fingerprint for identifying each material. In contrast, this was not possible with previous methods that utilized short wave infrared (SWIR) because black and other dark colored plastics typically absorb infrared radiation and no response could be recorded in either transmission or reflection. Accordingly, the use of terahertz waves can provide one or more benefits over these previous SWIR techniques.

While the above description includes a number of exemplary embodiments, many modifications, substitutions, changes and equivalents will be obvious to persons having ordinary skill in the art.

The invention claimed is:

1. A terahertz-based material identification system comprising:
   a) at least one terahertz source for transmitting a terahertz wave for interaction with an object, the interaction resulting in a resulting terahertz wave that is influenced by the object;
   b) at least one terahertz detector for receiving the resulting terahertz wave, the terahertz detector being configured to output measurement data corresponding to the resulting terahertz wave;
   c) a database containing known response signatures, wherein the known response signatures correspond to a plurality of different dark colored materials; and
   d) a processor in communication with the terahertz detector and the database, the processor being configured to:
      i) receive the measurement data;
      ii) calculate an object response signature based on the measurement data; and
      iii) compare the object response signature to the known response signatures so as to identify the object by determining whether the object is one of the plurality of different dark colored materials.

2. The material identification system of claim 1, wherein the resulting terahertz wave comprises one of:
   a) a transmitted terahertz wave that is transmitted through the object; or
   b) a reflected terahertz wave that is reflected from the object or from surroundings around the object.

3. The material identification system of claim 2, wherein the resulting terahertz wave is the transmitted terahertz wave, and the terahertz source and the terahertz detector are configured to operate in transmission mode, and wherein the terahertz detector is arranged to detect the transmitted terahertz wave.

4. The material identification system of claim 2, wherein the resulting terahertz wave is the reflected terahertz wave, and the terahertz source and the terahertz detector are configured to operate in reflection mode; and wherein the terahertz detector is arranged to detect the reflected terahertz wave.

5. The material identification system of claim 1, wherein the known response signatures correspond to a plurality of polymer materials, wherein the polymer materials include any one or more of black high-impact polystyrene (Black HIPS), black polycarbonate (Black PC), black polystyrene (Black PS), black acrylonitrile butadiene styrene (Black ABS), black polycarbonate acrylonitrile butadiene styrene (Black PC-ABS), black polystyrene (Black PS), black acrylic, and black ACETAL.

6. The material identification system of claim 1, wherein the processor is in communication with the terahertz source for operating the terahertz source over a range of terahertz frequencies and the object response signature is calculated over the range of terahertz frequencies.

7. The material identification system of claim 1, wherein the terahertz wave has a frequency of less than about 10-terahertz.

8. The material identification system of claim 1, wherein the terahertz wave has a frequency of between about 20-GHz and about 4-THz.

9. The material identification system of claim 1, further comprising a conveyor for conveying a mixture of objects through the terahertz wave transmitted by the terahertz source.

10. The material identification system of claim 1, further comprising an array of the terahertz sources and the terahertz detectors arranged in series or in parallel.

11. A terahertz-based sorting system comprising:
   a) a conveyor for conveying a mixture of objects;
   b) at least one terahertz source for transmitting a terahertz wave for interaction with at least one of the objects within the mixture, the interaction resulting in a resulting terahertz wave that is influenced by the object;
   c) at least one terahertz detector for receiving the resulting terahertz wave, the terahertz detector being configured to output measurement data corresponding to the resulting terahertz wave;
   d) a database containing known response signatures, wherein the known response signatures correspond to a plurality of different dark colored materials;
   e) a processor in communication with the terahertz detector and the database, the processor being configured to:
      i) receive the measurement data;
      ii) calculate an object response signature based on the measurement data; and
      iii) compare the object response signature to the known response signatures so as to identify the object by determining whether the object is one of the plurality of different dark colored materials; and
   f) a sorting device in communication with the processor for selectively separating the object from the mixture based on the identity of the object.

12. The sorting system of claim 11, wherein the known response signatures correspond to a plurality of polymer materials, and wherein the polymer materials include any one or more of black high-impact polystyrene (Black HIPS), black polycarbonate (Black PC), black polystyrene (Black PS), black acrylonitrile butadiene styrene (Black ABS), black polycarbonate acrylonitrile butadiene styrene (Black PC-ABS), black polystyrene (Black PS), black acrylic, and black ACETAL.

13. The terahertz-based sorting system of claim 11, further comprising an array of the terahertz sources and the terahertz detectors arranged in series or in parallel.

14. A method of identifying materials, the method comprising:
   a) transmitting a terahertz wave for interaction with an object, the interaction resulting in a resulting terahertz wave that is influenced by the object;
   b) receiving the resulting terahertz wave;
   c) generating measurement data based on the resulting terahertz wave received;
   d) calculating an object response signature based on the measurement data;
   e) storing known response signatures, wherein the known response signatures correspond to a plurality of different dark colored materials; and
   f) comparing the object response signature to the known response signatures so as to identify the object by determining whether the object is one of the plurality of different dark colored materials.

15. The method of claim 14, wherein the known response signatures correspond to a plurality of polymer materials, and wherein the polymer materials include any one or more of black high-impact polystyrene (Black HIPS), black polycarbonate (Black PC), black polystyrene (Black PS), black acrylonitrile butadiene styrene (Black ABS), black polycarbonate acrylonitrile butadiene styrene (Black PC-ABS), black polystyrene (Black PS), black acrylic, and black ACETAL.

16. The method of claim 14, wherein the terahertz wave is transmitted over a range of terahertz frequencies and the object response signature is calculated over the range of terahertz frequencies.

17. The method of claim 14, wherein the terahertz wave has a frequency of less than about 10-terahertz.

18. The method of claim 17, wherein the terahertz wave has a frequency of between about 20-GHz and about 4-THz.

19. The method of claim 14, further comprising:
   a) conveying a mixture of objects through the terahertz wave so as to identify at least one of the objects in the mixture; and
   b) selectively separating the at least one object from the mixture based on the identity of the at least one object.

20. The method of claim 19, wherein the at least one object from the mixture being conveyed comprises at least one dark colored plastic.

* * * * *